United States Patent
Hassler et al.

(10) Patent No.: US 8,388,683 B2
(45) Date of Patent: Mar. 5, 2013

(54) METHOD AND ASSEMBLY OF A PYROLYTIC CARBON COMPONENT ATTACHED TO ANOTHER COMPONENT

(75) Inventors: Michel Hassler, Saint-Ismier (FR); Cécile Réal, Paris (FR)

(73) Assignee: Tornier, Montbonnot-Saint-Martin (FR)

( * ) Notice: Subject to any disclaimer, the term of this patent is extended or adjusted under 35 U.S.C. 154(b) by 299 days.

(21) Appl. No.: 12/337,343

(22) Filed: Dec. 17, 2008

(65) Prior Publication Data

US 2009/0143865 A1 Jun. 4, 2009

Related U.S. Application Data

(63) Continuation-in-part of application No. PCT/IB2007/001725, filed on Jun. 25, 2007.

(60) Provisional application No. 61/056,326, filed on May 27, 2008.

(30) Foreign Application Priority Data

Jun. 29, 2006 (FR) ...................................... 06 52712

(51) Int. Cl.
*A61F 2/28* (2006.01)
*A61F 2/40* (2006.01)

(52) U.S. Cl. .................................. 623/16.11; 623/19.11

(58) Field of Classification Search ............... 623/16.11, 623/19.11, 22.11, 22.14; *A61F 2/28*
See application file for complete search history.

(56) References Cited

U.S. PATENT DOCUMENTS

| 3,526,005 | A | | 9/1970 | Bokros et al. | |
|---|---|---|---|---|---|
| 3,707,006 | A | | 12/1972 | Bokros et al. | |
| 3,842,442 | A | * | 10/1974 | Kolbel | 623/19.12 |
| 4,005,163 | A | | 1/1977 | Bokros | |
| 4,166,292 | A | | 9/1979 | Bokros | |
| 5,405,399 | A | | 4/1995 | Tornier | |
| 5,458,647 | A | | 10/1995 | Brochier et al. | |
| 5,534,033 | A | | 7/1996 | Simpson | |
| 5,593,445 | A | | 1/1997 | Waits | |
| 5,702,447 | A | | 12/1997 | Walch et al. | |
| 5,780,119 | A | | 7/1998 | Dearnaley et al. | |
| 6,090,145 | A | | 7/2000 | Hassler et al. | |
| 6,280,476 | B1 | * | 8/2001 | Metzger et al. | 623/22.11 |

(Continued)

FOREIGN PATENT DOCUMENTS

| EP | 1365165 | 11/2003 |
|---|---|---|
| FR | 2680967 | 3/1993 |
| WO | 2006063363 | 6/2006 |

OTHER PUBLICATIONS

PCT International Search Report and Written Opinion for International Application No. PCT/IB2007/001725, mailed on Dec. 13, 2007, 15 pages.
Shui et al., "High-strength high-surface-area porous carbon made from submicron-diameter carbon filaments," Cabon, vol. 34, Issue 9, 1996, pp. 811-814.

(Continued)

*Primary Examiner* — Thomas J Sweet
*Assistant Examiner* — Jason-Dennis Stewart
(74) *Attorney, Agent, or Firm* — Faegre Baker Daniels LLP

(57) ABSTRACT

A prosthetic assembly and a method of assembling same. The prosthetic assembly includes a base component with at least one engagement surface. A pyrolytic carbon component includes at least one engagement surface. The pyrolytic carbon component is elastically deformed to mechanically interlock with the engagement surface on the base component. The pyrolytic carbon component retains at least a portion of the deformation stress created during coupling with the base component.

15 Claims, 3 Drawing Sheets

U.S. PATENT DOCUMENTS

| | | | |
|---|---|---|---|
| 6,436,146 | B1 | 8/2002 | Hassler et al. |
| 7,182,787 | B2 | 2/2007 | Hassler et al. |
| 2003/0208276 | A1 | 11/2003 | Berelsman et al. |
| 2004/0030401 | A1* | 2/2004 | Hassler et al. ............. 623/22.46 |
| 2006/0069443 | A1* | 3/2006 | Deffenbaugh et al. .... 623/19.11 |
| 2007/0032878 | A1* | 2/2007 | Bader et al. ................ 623/22.17 |
| 2007/0156250 | A1 | 7/2007 | Seitz, Jr. et al. |
| 2007/0213833 | A1* | 9/2007 | Mears et al. ............... 623/23.11 |

OTHER PUBLICATIONS

Commercial brochure entitled "Scaphoid Partial Implant: An alternative to arthrodesis," presented at a Paris trade fair on Dec. 12, 1996, 2 pages.

J.P. Pequignot et al., "Partial Prosthesis of Scaphoid from Silastic to Pyrocarbon," Fourth congress of F.E.S.S.H., Bologna, Italy, Jun. 1997.

* cited by examiner

METHOD AND ASSEMBLY OF A PYROLYTIC CARBON COMPONENT ATTACHED TO ANOTHER COMPONENT

CROSS REFERENCE TO RELATED APPLICATIONS

This application is a continuation-in-part of International application no. PCT/IB2007/001725, with an international filing date of Jun. 25, 2007, entitled Assembly Between a Part Made of Pyrolytic Carbon and Another Part (Assemblage D'Une Piece En Pyrocarbone Et D'Une Autre Piece), which claims priority to French application no. 0652712, filed Jun. 29, 2006, the disclosures of which are all hereby incorporated by reference. This application also claims the benefit of U.S. provisional application No. 61/056,326, filed May 27, 2008, entitled Assembly Between a Part Made of Pyrolytic Carbon and Another Part, the disclosure of which is hereby incorporated by reference.

FIELD OF THE INVENTION

The present invention relates to a prosthesis with a pyrolytic carbon component attached to a substrate, and to a method of assembling such a prosthesis.

BACKGROUND OF THE INVENTION

Pyrolytic carbon is a material that has thus far been used to great satisfaction in the field of medical prostheses. One of the interesting properties of pyrolytic carbon is its Young's modulus is close to that of bone as well as its low coefficient of friction. As a result, pyrolytic carbon may work in frictional contact with bone without causing significant wear.

Yet pyrolytic carbon has the drawback of being poorly adapted as component of an assembly. On account of its brittleness it is difficult to attach pyrolytic carbon components using fasteners or welding. Nor can it be drilled as easily as other materials such as metals. For this reason, very few methods have been proposed thus far for joining a pyrolytic carbon component to another component in an assembly.

U.S. Pat. No. 5,458,647 describes an assembly that consists of a pyrolytic carbon cylinder force-fit into a bore in a metal component shorter than the cylinder. In this assembly, the pyrolytic carbon is permanently kept under stress. The danger exists, therefore, that the pyrolytic carbon will break when it is subjected to additional stresses during use. Moreover, the region of the junction between the component of the pyrolytic carbon cylinder engaged in the bore and the component situated outside of the bore constitutes a fragile region that may cause rupture of the pyrolytic carbon.

EP 1 365 165 discloses another type of assembly where a pyrolytic carbon component is shaped as a concave cone into which a convex cone of another component is fitted. One surface of the concave component perpendicular to the axis of the cones is abutting a corresponding surface of the convex component in order to account for the poor tensile strength of pyrolytic carbon, and thus limit the tensile stress of the concave component. This assembly also keeps the pyrolytic carbon permanently under stress. Moreover, the convex and concave cones must have a bearing surface sufficiently long for a good hold of the convex cone within the concave cone, as in all conical couplings. Such an assembly may thus not be realized when the pyrolytic carbon concave component has a small height.

U.S. Pat. No. 5,593,445 discloses a prosthesis with a pyrolytic carbon annular component snap-fit onto a spherical head of a convex component. The spherical head and the pyrolytic carbon annular component are engaged into a shell-shaped concave component. The convex and concave components are made of a titanium alloy or of ceramics. The annular pyrolytic carbon component is free to move on the spherical head but is held onto this head by the snap-fit arrangement. The convex and concave components are articulated like a ball-and-socket joint, and both are able to slide on the annular pyrolytic carbon component placed between them. This assembly of convex and concave components made of a material other than pyrolytic carbon and an intermediate mobile component made of pyrolytic carbon produces important friction, and thus risks of wear.

BRIEF SUMMARY OF THE INVENTION

The present invention relates to a method of assembling a pyrolytic carbon component to a substrate, and to a prosthesis with a pyrolytic carbon articular surface. The pyrolytic carbon component can be used to resurface the other component. In this new function the pyrolytic carbon component is fixed onto or into the other component while being subject to minimal or no stresses. The components are preferably shaped so that they may be snap fit together relying on elastic deformation of the pyrolytic carbon component. After assembly the pyrolytic carbon component preferably remains subject to some deformation stresses resulting from the snap fit engagement with the other component.

In one embodiment, the prosthetic assembly includes a base component with at least one engagement surface. The pyrolytic carbon component includes at least one engagement surface. The pyrolytic carbon component is elastically deformed to mechanically interlock with the engagement surface on the base component. The pyrolytic carbon component retains at least a portion of the deformation stress created during coupling with the base component. The elastic deformation may be isolated to the engagement surface or may extend partially or completely through the pyrolytic carbon component.

The base component is preferably made from a material having a Young's modulus higher than the pyrolytic carbon component. The base component can be a unitary component, typically of metal.

In one embodiment, the pyrolytic carbon component includes a convex articular surface, a concave inner surface, and at least one extension on a perimeter edge of the articular surface mechanically interlocked with the engagement surface on the base component. In another embodiment, the pyrolytic carbon component includes a concave articular surface, a convex inner surface, and at least one extension on a perimeter edge of the articular surface mechanically interlocked with the engagement surface on the base component.

In one embodiment, the engagement surface on the base component includes a maximum dimension and the engagement surface on the pyrolytic carbon component includes a minimum dimension that is less than the maximum dimension on the base member. The pyrolytic carbon component is optionally a resurfacing shell extending substantially across an outer surface of the base component. The pyrolytic carbon component is preferably an articular surface for a prosthetic implant. In one embodiment, the prosthetic implant is a shoulder prosthesis.

The present invention is also directed to a method of assembling a prosthetic implant. The method includes positioning at least one engagement surface on a pyrolytic carbon component opposite at least one engagement surface on a base component. The pyrolytic carbon component is elastically deformed. The pyrolytic carbon component is permitted to at least partially resume its original shape while engaged with the base component. The engagement surface on the pyrolytic carbon component mechanically interlocks with the engagement surface on the base component. At least a portion of the deformation stress in the pyrolytic carbon component created during coupling is retained in the base component.

The method includes implanting the prosthetic implant into a patent and orienting an articular surface on the pyrolytic carbon component into engagement with a bone.

BRIEF DESCRIPTION OF THE SEVERAL VIEWS OF THE DRAWING

Other features and advantages of the present invention will become apparent by reading the following detailed description where reference is made to the annexed drawings.

DETAILED DESCRIPTION OF THE INVENTION

Figure 1:
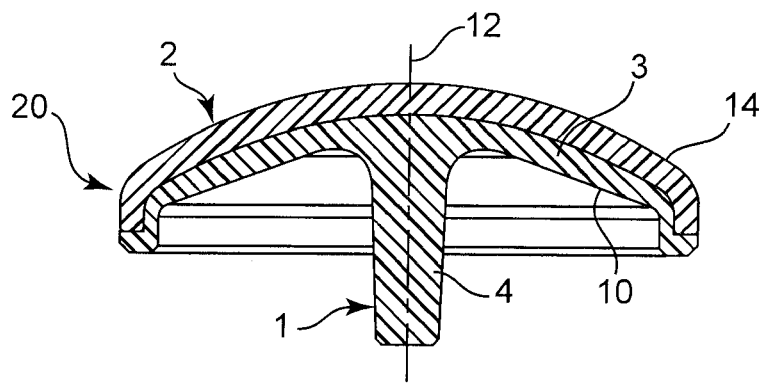
FIG. 1 is a sectional view of a shoulder prosthesis assembly including a pyrolytic carbon component with a concave surface engaged to a convex base component according to an embodiment of the present invention.

FIG. 1 illustrates a shoulder prosthesis 20 including a metal base component 1 with a convex outer surface 5 coupled to pyrolytic carbon component 2. The pyrolytic carbon component 2 includes a convex articular surface 14 and a concave inner surface 22 that couples with the outer surface 5 of the component 1.

In the illustrated embodiment, the convex metal base component 1 includes a cap 3 and a clamping cone 4 extending from the inner surface 10 of cap 3 along assembly axis 12 of component 1. In one embodiment, the clamping cone 4 is intended to be joined with a concave cone of a thread screw (not shown) fixed in the humerus. The base component 1 can be constructed from a variety of materials, such as for example, a cobalt-chromium alloy, ceramics, plastics, or composites thereof. In one embodiment, the base component 1 formed from a single homogeneous piece of material as a unitary component.

The pyrolytic carbon component 2 is a resurfacing shell that covers and hugs outer surface 5 of the metal cap 3. The pyrolytic carbon component 2 includes the convex outer articulation surface 14 of the prosthesis 20. In the illustrated embodiment, the surface 14 is intended to be in frictional contact with the humeral socket. It will be appreciated that an articular surface of pyrolytic carbon, such as the articular surface 14, has application in may joints within the body. Other applications of pyrolytic carbon in joints are found in U.S. Pat. Nos. 7,182,787 (Hassler et al.); 6,436,146 (Hassler et al.); 6,090,145 (Hassler et al.); and 5,405,399 (Tornier), all of which are incorporated by reference.

The pyrolytic carbon component 2 typically comes in the shape of a graphite substrate with a pyrolytic carbon layer deposited on it. Alternatively, component 2 could be made of solid pyrolytic carbon.

The pyrolytic carbon component 2 is preferably mechanically interlocked to the metal component 1. Such an assembly is made possible by the elasticity of pyrolytic carbon, more precisely of the pyrolytic carbon/graphite pair. This elasticity allows component 2 to undergo substantial deformation without any risk of plastic deformation. Once in position, the pyrolytic carbon at least partially returns to its original shape, creating a mechanical interlock with the metal component 1. As used herein, "mechanical interlock" or "mechanically interlocked" refers to elastic deformation of a first component during assembly with a second component to mechanically couple the two components together. After assembly the two components can typically only be separated by deformation, destruction, or disassembly of one of the components. In the illustrated embodiment, the pyrolytic carbon component 2 is elastically deformed and then permitted to at least partially resume its original shape while engaged with the base component 1. After assembly the pyrolytic carbon component 2 is preferably subjected to at least a portion of the deformation stresses created during assembly with the base component 1.

Figure 2:
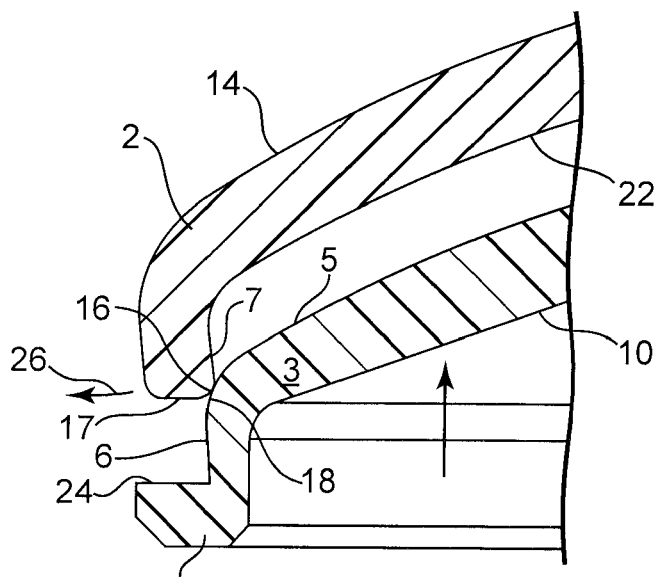
FIGS. 2 to 4 schematically illustrate one embodiment for assembling the convex and concave components of FIG. 1.
Figure 3:
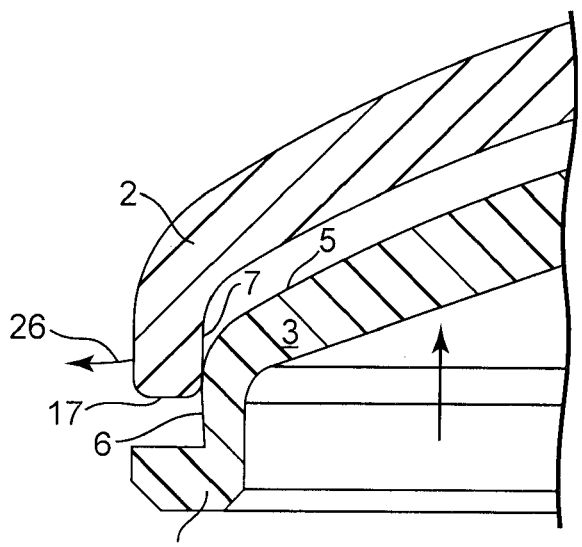
Figure 4:
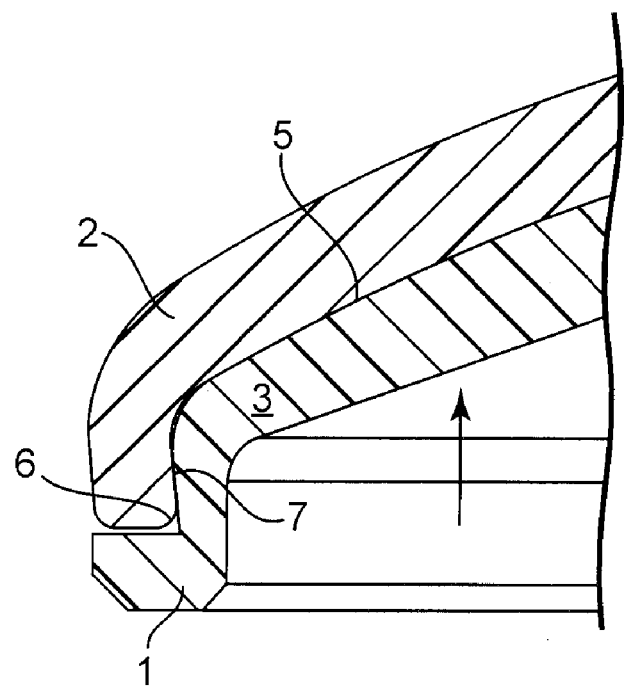

The method of assembling the components 1 and 2 is illustrated in FIG. 2 through FIG. 4. As shown in these Figures, cap 3 of the convex metal component 1 includes a convex upper outside surface 5. The cap 3 includes at least one engagement surface 6 and the pyrolytic carbon component 2 includes at least one engagement surface 7. In the illustrated embodiment, the engagement surfaces 7 are located on extension 15 of the component 2.

The illustrated engagement surfaces 6 and 7 are circular, so the maximum and minimum dimensions of the engagement surfaces 6 and 7, respectively, are respective diameters. The minimum diameter of the engagement surface 7 is less than the maximum diameter of the engagement surface 6. Consequently, engagement of the pyrolytic carbon component 2 with the base component 1 along the assembly axis 12 results in deformation of the pyrolytic carbon component 2. In an alternate embodiment, the engagement surfaces 6 and 7 can be a variety of non-circular shapes, such as for example oval or octagonal.

Figure 5:
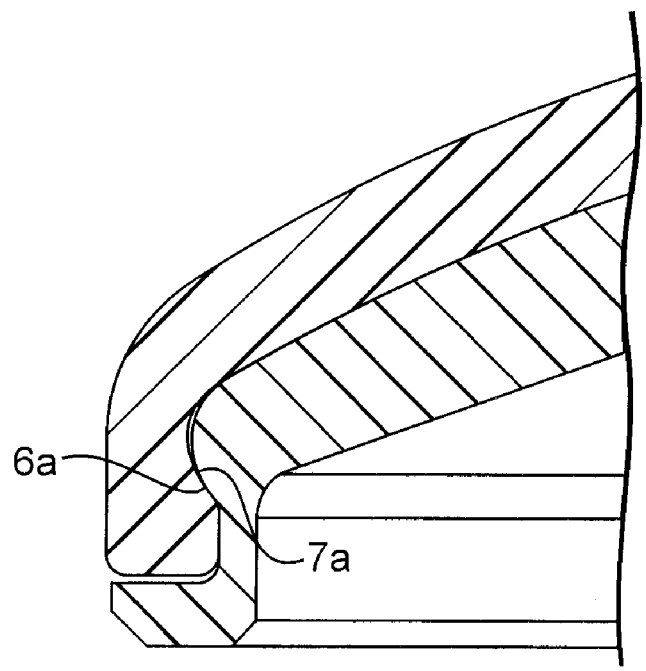
FIG. 5 is a sectioned view of an alternate prosthesis assembly including a pyrolytic carbon component with a concave surface engaged to a convex base component according to an embodiment of the present invention.

In the illustrated embodiment, the engagement surfaces 6 and 7 are frustum-shaped. The engagement surface 7 includes a minimum diameter at the distal edge 16 that tapers outward (i.e., the diameter increases) moving toward the articular surface 14, as measure relative to the assembly axis 12. By contrast, the engagement surface 6 has a maximum diameter at the rim 18, which tapers inward (i.e., the diameter decreases) moving toward the surface 24, as measured relative to assembly axis 12. As best illustrated in FIG. 5, the engagement surface 6 mechanically interlocks with the engagement surface 7. The components 1 and 2 can not be separated without deformation or destruction of one of the components 1, 2.

At the beginning of insertion of the convex component 1 into the concave component 2, the rim 18 of the upper surface 5 of the convex component 1 exerts high stresses on distal edges 16 of the concave component 2 in order to widen it (FIG. 2). During this phase the concave component 2 may undergo deformation in direction 26 up to a stage close to rupture or fracture of the pyrolytic carbon. The deformation of the concave component 2 remains elastic throughout, since pyrolytic carbon has no plastic domain (its elastic limit corresponds generally to its rupture limit). Thus widened, the concave component 2 then slides over the lateral frustum-shaped engagement surface 6 of convex component 1 (FIG. 3). As this sliding motion continues, which is facilitated by the low coefficient of friction of pyrolytic carbon, the stresses produced at the distal edge 16 of the concave component 2 diminish. The elastic deformation may be isolated to the engagement surface 6, 7 or may extend partially or completely through the pyrolytic carbon component 2.

Insertion of the convex component 1 into the concave component 2 stops when the inner surface 22 of concave component 2 comes into abutment with the upper surface 5 of convex component 1. At this point stress on the concave component 2 is reduced or eliminated, and the elastic nature of the pyrolytic carbon causes the concave component 2 to resume a shape closer to its initial shape before engagement with the convex component 1 (FIG. 4), resulting in a mechanical interlock between the components 1, 2.

In an alternate embodiment, distal edges 17 on the component 2 abut surface 24 on the component 1. In one embodiment, a gap exists between the outer surface 5 of the component 1 and the inner surface 22 of the component 2. The gap permits some flexure of the outer articular surface 14 of the component 2 relative to the surface 5 on the component 1.

According to one embodiment, in this final position of assembly the concave component 2 remains subject to deformation stresses resulting from the mechanical coupling with the convex component 1. In other words, concave component 2 is maintained in a slightly widened state by convex component 1, so that components 1 and 2 are locked together by clamping action. The concave component 2 may thus provide a resurfacing function for convex component 1.

In this same final assembly position, the lateral frustum-shaped engagement surface 6 of convex component 1 cooperates with a corresponding inner frustum-shaped engagement surface 7 of concave component 2 to bias the convex component 1 into engagement with the component 2. As a result, the engagement surface 7 tapers inward in a direction moving away from the convex articular surface 14, creating an interlocking engagement with the engagement surface 6 on the convex component 1. Surfaces 6, 7 are not necessarily rigorously frustum-shaped. In one embodiment, the surfaces 6, 7 may have slightly rounded profiles. The assembly illustrated in FIG. 4 is reversible. By adjusting the slope of surfaces 6 and 7 it is possible to make disassembly of the convex and concave components more or less difficult. In yet another embodiment, the surfaces 6 and 7 can be configured parallel to the assembly axis 12.

FIG. 5 shows a variant in which the slope of the frustum-shaped surfaces designated by 6a and 7a is emphasized, which makes a disassembly of the convex and concave components more difficult. For example, surfaces 6a and 7a may be configured with undercuts, detents, recesses, and the like, to mechanically interlock the concave component 2 to the convex component 1. In one embodiment, the undercuts create a snap-fit engagement between the components 1, 2. In another variant the assembly could be made permanent by replacing the frustum-shaped surfaces 6a and 7a by surfaces perpendicular to the assembly axis 12.

Components 1 and 2 may have a great variety of shapes, since the concave component 2 is not intended to be mobile relative to the convex component 1. More particularly, the assembly according to the invention is fit, both for concave components having small height (relative to their diameter or radius), like the component 2 shown, and for concave components of greater height.

It will be appreciated that the assembly mode according to the invention constitutes a solution for resurfacing a metal component with pyrolytic carbon, for instance. Depositing pyrolytic carbon on metal is technically difficult, since metals will not resist the conditions of temperature under which pyrolytic carbon deposits are produced.

It will be noticed in addition that, once assembled with the convex component, the pyrolytic carbon concave component is subject to stresses that are lower than those to which it is subjected during insertion of the convex component, so the concave component will be able to withstand additional stresses while the assembly is in function, typically stresses exerted onto the prosthesis by the neighboring bones while the patient moves. Thus, the risk of rupture of the pyrolytic carbon during the functioning of the assembly is reduced.

Although the convex component 1 is typically metal, it could be made from another material, for instance from ceramic, plastics, or composites thereof. More generally, the material from which the convex component is made preferably has a Young's modulus superior to that of pyrolytic carbon.

Figure 6:
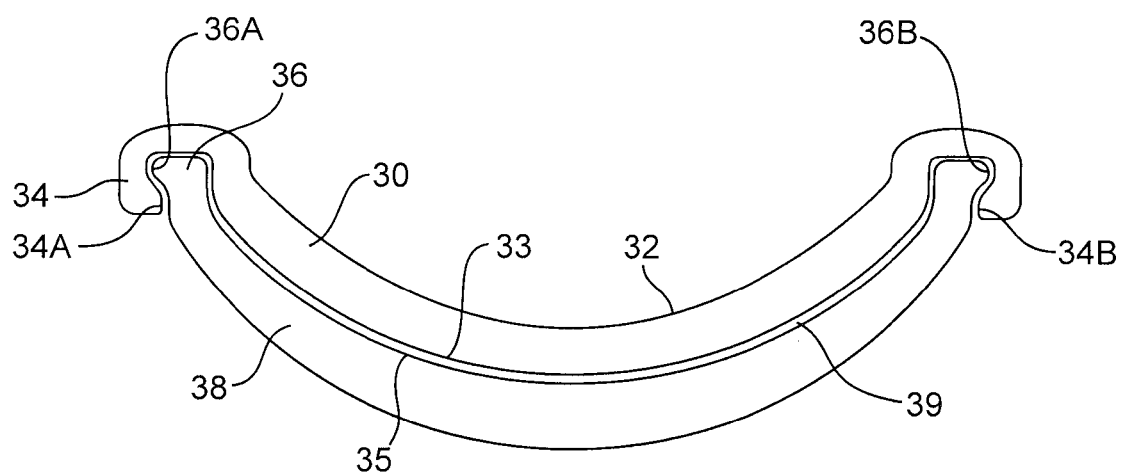
FIG. 6 is a sectioned view of an alternate prosthesis assembly including a pyrolytic carbon component with a convex surface engaged to a concave base component according to an embodiment of the present invention.

Finally, the present invention is not limited to the assembly of a pyrolytic carbon concave component with a convex component. FIG. 6 illustrates an alternate embodiment in which the pyrolytic carbon component 30 includes a concave articular surface 32 and a convex surface 33 shaped to engage with concave surface 35 of base component 38. In the illustrated embodiment, the component 30 includes projections 34 around a perimeter edge of the concave articular surface 32 that deflect elastically to form a snap-fit relationship with distal edges 36 of base component 38. The projections 34 may include a frustoconical taper, as discussed above, or other features such as detents, undercuts, and the like, to mechanically interlock the component 30 to the base component 38.

The maximum dimension between the locations 36A, 36B on the distal edges 36 is preferably greater then the minimum dimension between the locations 34A, 34B on the projections 34. During assembly, the projections 34 are elastically deformed and then permitted to at least partially resume their original shape while engaged with the base component 38, creating a mechanical interlock between the components 30, 38.

In one embodiment, the convex surface 33 abuts the concave surface 35. In an alternate embodiment, a gap 39 is maintained between the surfaces 33, 35 that permits the pyrolytic carbon component 30 to flex or deform within the confines of the base component 38.

Where a range of values is provided, it is understood that each intervening value, to the tenth of the unit of the lower limit unless the context clearly dictates otherwise, between the upper and lower limit of that range and any other stated or intervening value in that stated range is encompassed within the inventions. The upper and lower limits of these smaller ranges which may independently be included in the smaller ranges is also encompassed within the inventions, subject to any specifically excluded limit in the stated range. Where the stated range includes one or both of the limits, ranges excluding either both of those included limits are also included in the inventions.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present inventions are not entitled to antedate such publication by virtue of prior invention. Further, the dates of publication provided may be different from the actual publication dates which may need to be independently confirmed.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the components disclosed embodiments described above.

Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims.

What is claimed is:

1. A prosthetic assembly comprising:
a base component comprising at least one engagement surface; and
a pyrolytic carbon component comprising at least one engagement surface, the pyrolytic carbon component being configured to elastically deform from a first shape upon pressing the pyrolytic carbon component onto the base component and then partially return to the first shape such that the engagement surface of the pyrolytic carbon component mechanically interlocks with the engagement surface of the base component in a snap fit relationship with at least a portion of the deformation stress, created during coupling with the base component, begin retained by the pyrolytic carbon component so as to immobilize the base component and the pyrolytic carbon component with respect to each other.

2. The prosthetic assembly of claim 1 wherein the base component comprises a material having a Young's modulus higher than the pyrolytic carbon component.

3. The prosthetic assembly of claim 1 wherein the base component comprises a unitary component.

4. The prosthetic assembly of claim 1 wherein the base component comprises metal.

5. The prosthetic assembly of claim 1 wherein the pyrolytic carbon component comprises:
a convex articular surface;
a concave inner surface; and
at least one extension on a perimeter edge of the articular surface mechanically interlocked with the engagement surface on the base component in the snap fit relationship.

6. The prosthetic assembly of claim 1 wherein the pyrolytic carbon component comprises:
a concave articular surface;
a convex inner surface; and
at least one extension on a perimeter edge of the articular surface mechanically interlocked with the engagement surface on the base component in the snap fit relationship.

7. The prosthetic assembly of claim 1, wherein the engagement surface on the base component comprises a maximum dimension and the engagement surface on the pyrolytic carbon component comprises a minimum dimension that is less than the maximum dimension on the base member.

8. The prosthetic assembly of claim 1 wherein the pyrolytic carbon component comprises a resurfacing shell extending substantially across an outer surface of the base component.

9. The prosthetic assembly of claim 1 wherein the pyrolytic carbon component comprises an articular surface for a prosthetic implant.

10. The prosthetic assembly of claim 1 comprising a shoulder prosthesis.

11. The prosthetic assembly of claim 1, wherein the base component includes a perimeter portion having an inner side and an outer side, the inner side comprising the at least one engagement surface and the pyrolytic carbon component includes a perimeter portion having an inner side and an outer side, the outer side comprising the at least one engagement surface.

12. The prosthetic assembly of claim 1, wherein the mechanical interlock between the base component and the pyrolytic carbon component is reversible, so as to permit removal of the pyrolytic carbon component from the base component.

13. A prosthetic assembly having a first side, a second side, and a longitudinal axis extending between the first and second sides, the prosthetic assembly comprising:
a base component having an outer surface toward the first side of the prosthetic assembly and comprising at least one engagement surface facing outward relative to the longitudinal axis and having a rim proximal to the outer surface of the base component, the engagement surface of the base component having a maximum dimension at the rim and tapering inward relative to the longitudinal axis moving away from the outer surface toward the second side of the prosthetic assembly; and
a pyrolytic carbon component comprising at least one engagement surface and an articular surface toward the first side of the prosthetic assembly, the engagement surface of the pyrolytic carbon component having a distal edge defining a minimum dimension, the engagement surface tapering outward relative to the longitudinal axis moving away from the distal edge toward the first side of the prosthetic assembly, the pyrolytic carbon component elastically being deformed and maintained in a widened state by the engagement surface of the base component to mechanically interlock with the engagement surface on the base component.

14. The prosthetic assembly of claim 13 wherein the minimum dimension of the pyrolytic carbon component is less than the maximum dimension of the base member.

15. The prosthetic assembly of claim 13, wherein the mechanical interlock between the base component and the pyrolytic carbon component is reversible, so as to permit removal of the pyrolytic carbon component from the base component.

* * * * *